(12) United States Patent
Shinno et al.

(10) Patent No.: US 7,641,785 B2
(45) Date of Patent: Jan. 5, 2010

(54) METHOD OF MEASURING BLOOD COMPONENT AND SENSOR USED IN THE METHOD

(75) Inventors: Teppei Shinno, Matsuyama (JP); Shin Ikeda, Katano (JP)

(73) Assignee: Panasonic Corporation, Osaka (JP)

( * ) Notice: Subject to any disclaimer, the term of this patent is extended or adjusted under 35 U.S.C. 154(b) by 797 days.

(21) Appl. No.: 10/954,020

(22) Filed: Sep. 28, 2004

(65) Prior Publication Data

US 2005/0145490 A1 Jul. 7, 2005

(30) Foreign Application Priority Data

Oct. 2, 2003 (JP) ............................. 2003-344761

(51) Int. Cl.
*G01N 27/327* (2006.01)

(52) U.S. Cl. ................................ 205/777.5; 204/403.12

(58) Field of Classification Search ........................ None
See application file for complete search history.

(56) References Cited

U.S. PATENT DOCUMENTS

| | | | | |
|---|---|---|---|---|
| 5,487,978 | A * | 1/1996 | DeCastro et al. | 435/11 |
| 5,650,062 | A * | 7/1997 | Ikeda et al. | 205/778 |
| 5,942,102 | A * | 8/1999 | Hodges et al. | 205/778 |
| 6,287,451 | B1 * | 9/2001 | Winarta et al. | 205/777.5 |
| 6,377,896 | B1 | 4/2002 | Sato et al. | |
| 6,632,349 | B1 * | 10/2003 | Hodges et al. | |
| 6,773,564 | B1 | 8/2004 | Yugawa et al. | |
| 2002/0179442 | A1 | 12/2002 | Miyazaki et al. | |
| 2003/0159945 | A1 | 8/2003 | Miyazaki et al. | |
| 2004/0079652 | A1 * | 4/2004 | Vreeke et al. | 205/777.5 |

FOREIGN PATENT DOCUMENTS

| | | |
|---|---|---|
| JP | 11-194108 | 7/1999 |
| JP | 2000-171428 | 6/2000 |
| JP | 2001-516039 | 9/2001 |
| JP | 2002-207022 | 7/2002 |
| JP | 2002-357583 | 12/2002 |
| JP | 2003-156469 | 5/2003 |
| WO | 99/13100 | 3/1999 |
| WO | WO 02/44705 A1 | 6/2002 |
| WO | 03/067252 | 8/2003 |
| WO | WO 2005003774 A1 * | 1/2005 |

* cited by examiner

*Primary Examiner*—Nam X Nguyen
*Assistant Examiner*—Kourtney R Salzman
(74) *Attorney, Agent, or Firm*—Hamre, Schumann, Mueller & Larson, P.C.

(57) ABSTRACT

A sensor for blood component analysis that can correct the effect of a hematocrit easily is provided. The sensor includes an analysis portion including a working electrode, a counter electrode, and a reagent portion. The reagent portion includes an oxidoreductase that reacts with the blood component and a mediator, and the blood component is measured by causing a redox reaction between the blood component and the oxidoreductase in the presence of the mediator and detecting a redox current generated by the redox reaction by the working electrode and the counter electrode. In this sensor, the reagent portion further includes a hemolyzing agent (e.g., sodium cholate) for hemolyzing an erythrocyte, and when detecting the redox current, the erythrocyte is hemolyzed with the hemolyzing agent so as to cause hemoglobin released to an outside of the erythrocyte to react with the mediator and a current generated by this reaction also is detected to correct an effect of a hematocrit.

21 Claims, 5 Drawing Sheets

METHOD OF MEASURING BLOOD COMPONENT AND SENSOR USED IN THE METHOD

BACKGROUND OF THE INVENTION

1. Field of the Invention

The present invention relates to a method of measuring a blood component and a sensor used in the method.

2. Related Background Art

Conventionally, sensors for blood component measurement have been used for clinical test, self-measurement of blood glucose level by diabetics, etc. The configuration of the sensor for blood component measurement is such that, for example, a cover is disposed on an insulating substrate having a working electrode and a counter electrode on its surface, with a spacer intervening between the cover and the insulating substrate. On the working electrode and the counter electrode, a reagent containing an oxidoreductase, a mediator (an electron carrier), and the like is provided, thereby forming an analysis portion. The analysis portion communicates with one end of a channel for leading blood to the analysis portion. The other end of the channel is open toward the outside of the sensor so as to serve as a blood supply port. Blood component analysis (e.g., analysis of blood glucose level) using the sensor configured as above is carried out in the following manner, for example. First, the sensor is set in a dedicated measuring device (a meter). Then, a fingertip or the like is injured with a lancet to cause bleeding, and the blood supply port of the sensor is brought into contact with the blood that has come out. The blood is drawn into the channel of the sensor by capillary action and flows through the channel to be led to the analysis portion where the blood comes into contact with the reagent. Then, a redox reaction occurs between a blood component and the oxidoreductase so that a current flows via the mediator. The working electrode and the counter electrode detect the current, and the measuring device converts the detected current into an amount of the blood component and displays the value obtained by the conversion.

In the above-described manner, the sensor can measure the blood component. However, since the obtained measured value might be affected by a hematocrit (Hct), it might be necessary to remove the effect of Hct in order to obtain an accurate measured value. One example of a method of removing the effect of Hct is preparing a correction table beforehand using a sample with a known Hct and then correcting the measured value using this correction table (see JP 11(1999)-194108 A, for example). Another example is correcting a Hct using a parameter that has been set beforehand (see WO 02/44705, for example). However, these methods require a laborious correction process such as providing a correction table beforehand or performing a complicated calculation using a parameter.

SUMMARY OF THE INVENTION

The present invention was made in light of the foregoing problems, and it is an object of the present invention to provide a method and a sensor that can measure a blood component without a laborious correction process.

In order to achieve the above object, the present invention provides a method of measuring a blood component, including: causing a redox reaction between the blood component and an oxidoreductase in the presence of a mediator; detecting a redox current generated by the redox reaction by electrodes; and converting the detected current value into an amount of the blood component, wherein when detecting the redox current, an erythrocyte is hemolyzed so as to cause hemoglobin released to an outside of the erythrocyte to react with the mediator and a current generated by this reaction also is detected to correct an effect of a hematocrit.

The present invention also provides a sensor for measuring a blood component, including an analysis portion, the analysis portion including: a working electrode; a counter electrode; and a reagent portion. The reagent portion includes an oxidoreductase that reacts with the blood component and a mediator, and the blood component is measured by causing a redox reaction between the blood component and the oxidoreductase in the presence of the mediator and detecting a redox current generated by the redox reaction by the working electrode and the counter electrode. In this sensor, the reagent portion further includes a hemolyzing agent for hemolyzing an erythrocyte, and when detecting the redox current, the erythrocyte is hemolyzed with the hemolyzing agent so as to cause hemoglobin released to an outside of the erythrocyte to react with the mediator and a current generated by this reaction also is detected to correct an effect of a hematocrit.

Note here that a greater Hct means a greater amount of hemoglobin. That means, when the erythrocyte is hemolyzed to cause the hemoglobin released to the outside of the erythrocyte to react with the mediator, the current generated by this reaction also is greater. Therefore, by detecting this current along with the current generated by the redox reaction of the blood component, even when the current generated by the redox reaction is smaller than the actual value due to the effect of the Hct, the current value that has been corrected to remove the effect of the Hct can be obtained by the electrodes. Thus, according to the present invention, by electrochemically detecting the blood component and also the hemoglobin that varies depending on Hct, the effect of Hct can be corrected automatically by performing current detection only once. Therefore, a complicated correction process is not necessary.

BRIEF DESCRIPTION OF THR DRAWINGS

DETAILED DESCRIPTION OF THE INVENTION

Figure 1A:
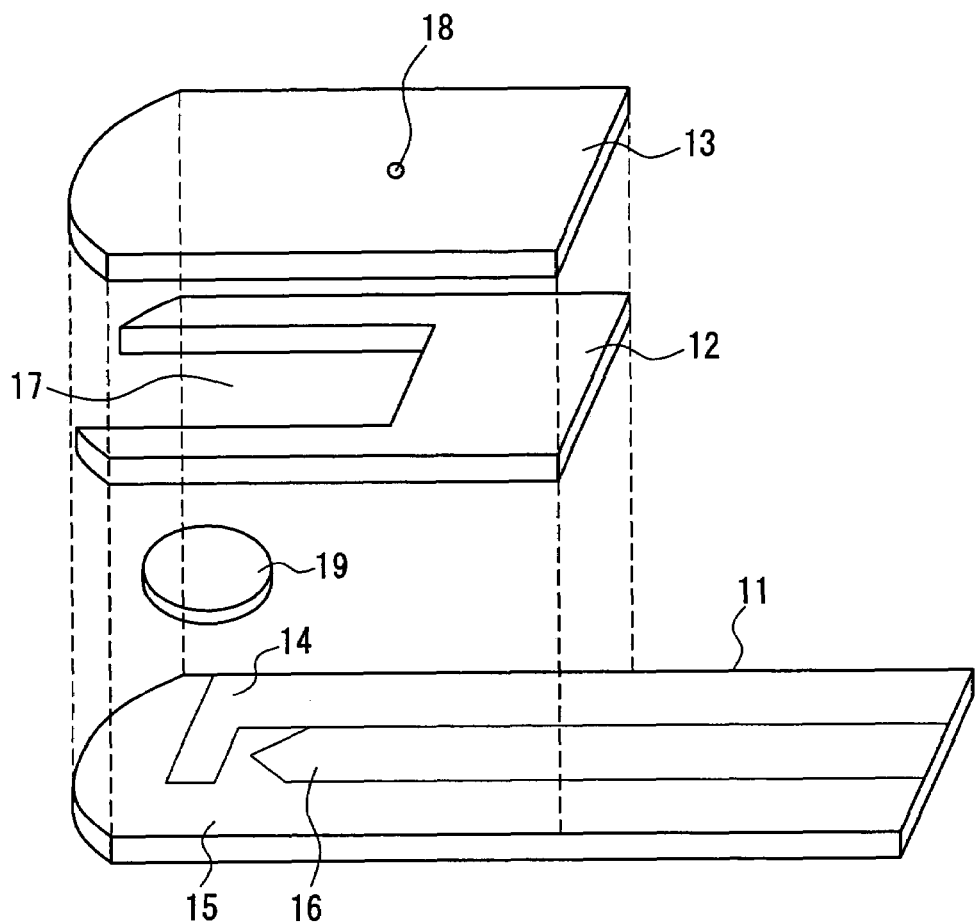
FIG. 1A is an exploded perspective view showing an example of a sensor according to the present invention.

Hereinafter, the present invention will be described in detail.

In the measurement method of the present invention, the hemolysis preferably is caused by a membrane protein solubilizer so as to allow the hemolysis to be caused in a simple manner without performing a laborious operation. However, in the present invention, means for causing the hemolysis is not limited thereto, and can be, for example, physical means such as an osmotic shock procedure using an anisotonic solution, an ultrasonic treatment, or a freezing and thawing method that causes hemolysis by repeating freezing and thawing.

In the measurement method and the sensor of the present invention, the membrane protein solubilizer is not particularly limited as long as it can hemolyze erythrocytes. Note here that the term "hemolysis" as used herein refers to a phenomenon in which a membrane of an erythrocyte is broken and hemoglobin and the like contained in the erythrocyte are release to the outside of the erythrocyte. Examples of the membrane protein solubilizer include lipase, saponins, lysozyme, inorganic salts, and detergents. Among them, detergents are more preferable. Examples of the detergents include ionic detergents such as anionic detergents, cationic detergents, and amphoteric detergents, nonionic detergents, and cholic acid-based detergents. Among them, cholic acid-based detergents are preferable in terms of simplicity in preparing a reagent and the crystal condition of a reagent portion. Examples of the cholic acid-based detergent include cholic acid, sodium cholate, cholic acid methyl ester, chenodeoxycholic acid, sodium chenodeoxycholate, diphenylglycolic acid (benzilic acid), deoxycholic acid, sodium deoxycholate, sodium glycochenodeoxycholate, glycocholic acid, sodium glycocholate, glycodeoxycholic acid, sodium glycodeoxycholate, glycolic acid, sodium glycolate, sodium glycolithocholate, lithocholic acid, sodium thioglycolate, sodium taurocholate, sodium taurodeoxycholate, sodium tauroursodeoxycholate, sodium ursodeoxycholate, and ursodeoxycholic acid. They may be used individually or two or more of them may be used together. Among the above-described cholic acid-based detergents, sodium cholate, sodium deoxycholate, sodium glycocholate, sodium glycodeoxycholate, sodium taurocholate, and sodium taurodeoxycholate are preferable, and sodium cholate, sodium glycocholate, sodium taurocholate, and sodium taurodeoxycholate are particularly preferable. In addition to the above-described detergents, the following detergents also can be used, for example: sodium lauryl sulfate (SDS); N,N-bis(3-D-gluconamidopropyl)cholamide (BIGCHAP); 3-[(3-cholamidopropyl)dimethylammonio]-1-propanesulfonate (CHAPS); N,N-bis(3-D-gluconamidopropyl)deoxycholamide (deoxy-BIGCHAP); 3-[(3-cholamidopropyl)dimethylammonio]-2-hydroxy-1-propanesulfonate (CHAPSO); n-decanoyl-N-methylglucamide (MEGA-10); n-nonanoyl-N-methylglucamide (MEGA-9); n-octanoyl-N-methylglucamide (MEGA-8); n-octyl-β-D-thioglucoside; n-octyl-β-D-maltoside; n-octyl-β-D-glucoside; sucrose monolaurate (SM1200); sucrose monocaprate (SM1000); and sucrose monocholate.

In the measurement method and the sensor of the present invention, the amount of the membrane protein solubilizer is not particularly limited, but may be, for example, 0.01 mM to 100 mM, preferably 0.1 mM to 50 mM, and particulaly preferably 0.2 mM to 2.0 mM per one measurement or one sensor.

In the measurement method and the sensor of the present invention, the mediator is not particularly limited. Examples of the mediator include potassium ferricyanide, p-benzoquinone, p-benzoquinone derivatives, phenazine methosulfate, methylene blue, ferrocene, and ferrocene derivatives. Among them, potassium ferricyanide is preferable. The amount of the mediator is not particularly limited, but may be, for example, 0.1 mM to 1000 mM, preferably 1 mM to 500 mM, and more preferably 5 mM to 200 mM per one sensor or one measurement.

In the measurement method and the sensor of the present invention, an analyte is not particularly limited as long as it is a blood component, and may be, for instance, glucose, lactic acid, uric acid, bilirubin, cholesterol, or the like. The oxidoreductase may be an oxidoreductase that reacts with a blood component as an analyte, and examples thereof include glucose oxidase, lactate oxidase, cholesterol oxidase, bilirubin oxidase, glucose dehydrogenase, and lactate dehydrogenase. The amount of the oxidoreductase may be, for example, 0.1 U to 100 U, preferably 0.5 U to 50 U, and more preferably 1 U to 10 U per one sensor or one measurement.

In the sensor of the present invention, it is preferable that the reagent portion further contains a hydrophilic polymer, an enzyme stabilizer, and a crystal homogenizing agent.

The hydrophilic polymer serves to impart viscosity to a reagent solution so that, when preparing the reagent portion by drying the reagent solution, a homogenous reagent portion is formed on the electrodes easily and the adhesion between the electrode and the reagent portion is enhanced. The hydrophilic polymer also serves to improve the crystal condition of the reagent portion after being dried. Examples of the hydrophilic polymer include carboxymethyl cellulose (CMC), hydroxyethyl cellulose, hydroxypropyl cellulose, methyl cellulose, ethylcellulose, ethyl hydroxyethyl cellulose, carboxyethyl cellulose, polyvinyl alcohol, polyvinylpyrrolidone, polyamino acid such as polylysine, polystyrene sulfonate, gelatin and derivatives thereof, polyacrylic acid and salts thereof, polymethacrylic acid and salts thereof, starch and derivatives thereof, maleic anhydride polymer and salts thereof, and agarose gel and derivatives thereof. They may be used individually or two or more of them may be used together. Among them, CMC is preferable. The ratio of the hydrophilic polymer to the entire reagent solution for preparing a reagent portion may be, for example, 0.001 wt % to 5 wt %, preferably 0.005 wt % to 2.5 wt %, and more preferably 0.01 wt % to 1.0 wt %.

As the enzyme stabilizer, sugar alcohol may be used. Examples of the sugar alcohol include chain polyhydric alcohols and cyclic sugar alcohols, such as sorbitol, maltitol, xylitol, mannitol, lactitol, reduced paratinose, arabinitol, glycerol, ribitol, galactitol, sedoheptitol, perseitol, volemitol, styracitol, polygalitol, iditol, talitol, allitol, inositol, hydrogenated glucose syrup, and isylitol. Note here that stereoisomers, substitution products, and derivatives of these sugar alcohols may also be used as the enzyme stabilizer. These sugar alcohols may be used individually or two or more of them may be used together. Among them, maltitol is preferable. The amount of the enzyme stabilizer may be, for example, 0.01 mM to 500 mM, preferably 0.05 mM to 100 mM, and more preferably 0.1 mM to 50 mM per one measurement or one sensor.

The crystal homogenizing agent serves to homogenize the crystal condition of the reagent portion. As the crystal homogenizing agent, an amino acid may be used, for example. Examples of the amino acid include glycine, alanine, valine, leucine, isoleucine, serine, threonine, methionine, asparagine, glutamine, arginine, lysine, histidine, phenylalanine, tryptophan, proline, sarcosine, betaine, taurine, and salts, substitution products, and derivatives of these amino acids. They may be used individually or two or more of them may be used together. Among them, glycine, serine, proline, threonine, lysine, and taurine are preferable, and taurine is more preferable. The amount of the crystal homogenizing agent may be, for example, 0.1 mM to 1000 mM, preferably 5 mM to 500 mM, and more preferably 10 mM to 300 mM per one measurement or one sensor.

Next, the configuration of the sensor of the present invention will be described. For example, in the sensor of the present invention, a working electrode and a counter electrode are disposed on an insulating substrate, thereby forming an analysis portion. A reagent portion further is disposed on the analysis portion. The analysis portion communicates with one end of a channel for leading blood to the analysis portion, and the other end of the channel is open toward the outside of the sensor, thereby allowing this opening to serve as a blood supply port. On the insulating substrate, a cover is disposed with a spacer intervening therebetween. Preferably, the sensor further includes a detecting electrode that is located farther from the blood supply port than the analysis portion so that whether or not blood is supplied to the analysis portion is detected by this detecting electrode.

Figure 1B:
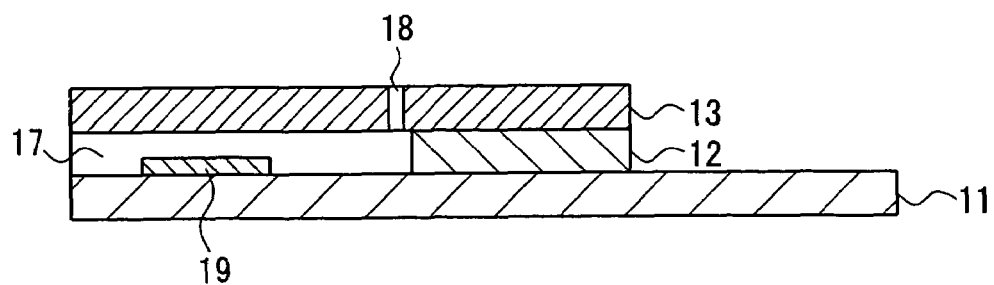
FIG. 1B is a cross-sectional view of the same.

FIG. 1 shows one example of the sensor of the present invention configured as above. FIG. 1A is an exploded perspective view of the sensor, and FIG. 1B is a cross-sectional view of the same. As shown in FIG. 1, in this sensor, a working electrode 14 and a counter electrode 15 are formed on an insulating substrate 11, and a reagent portion 19 is disposed on these electrodes, thereby forming an analysis portion. On the insulating substrate 11, a detecting electrode 16 further is formed, which is located farther from the blood inlet port side than the working electrode 14 and the counter electrode 15. The reagent portion 19 contains the oxidoreductase such as glucose oxidase as described above, the mediator as described above, a hemolyzing agent such as cholic acid, the hydrophilic polymer as described above, the enzyme stabilizer as described above, the crystal homogenizing agent as described above, and the like. The type and the blend ratio of these reagents are as described above. A cover 13 is disposed on the insulating substrate 11 so as to cover an entire area excluding one end portion (the end portion on the right in FIG. 1) with a spacer 12 intervening therebetween. The analysis portion communicates with a channel 17 for leading blood to the analysis portion. The channel 17 extends to the other end portion (the end portion on the left in FIG. 1) of the sensor, and the tip of the channel 17 on the other end portion side is open toward the outside of the sensor so as to serve as a blood inlet port. The working electrode 14, the counter electrode 15, and the detecting electrode 16 are connected to leads, respectively. These leads extend to the above-described one end portion of the sensor with the tip of each lead not being covered with the cover but being exposed. The cover 13 has an air vent hole 18 for enhancing the capillary action at a portion corresponding to the rear side of the channel 17.

In the present invention, the material for the insulating substrate is not particularly limited, and may be, for example, polyethylene terephthalate (PET), polycarbonate (PC), polyimide (PI), polyethylene (PE), polypropylene (PP), polystyrene (PS), polyvinyl chloride (PVC), polyoxymethylene (POM), monomer-cast nylon (MC), polybutylene terephthalate (PBT), polymethyl methacrylate (PMMA), an ABS resin (ABS), or glass. Among them, polyethylene terephthalate (PET), polycarbonate (PC), and polyimide (PI) are preferable, and polyethylene terephthalate (PET) is more preferable. The size of the insulating substrate is not particularly limited. For example, the insulating substrate may have an overall length of 5 mm to 100 mm, a width of 3 mm to 50 mm, and a thickness of 0.1 mm to 2 mm; preferably an overall length of 10 mm to 50 mm, a width of 3 mm to 20 mm, and a thickness of 0.2 mm to 1 mm; and more preferably an overall length of 15 mm to 30 mm, a width of 5 mm to 10 mm, and a thickness of 0.3 mm to 0.6 mm.

The electrodes and leads on the insulating substrate may be formed, for example, by forming a conductive layer with gold, platinum, palladium, or the like by sputtering or vapor deposition and then processing the conductive layer into a particular electrode pattern with a laser. Examples of the laser include YAG lasers, $CO_2$ lasers, and excimer lasers.

The reagent portion can be formed, for example, by dissolving a predetermined reagent in water or a buffer solution and then drying it. For example, in a 0.01 wt % to 2.0 wt % CMC aqueous solution, 0.1 U/sensor to 5.5 U/sensor of PQQ-GDH, 10 mM to 200 mM of potassium ferricyanide, 0.05 mM to 30 mM of maltitol, 10 mM to 300 mM of taurine, and 0.02 mM to 5.0 mM of sodium cholate are added and dissolved. The reagent portion can be formed by dropping the thus-obtained solution on the analysis portion (on the working electrode and the counter electrode) of the substrate and then drying it. The drying may be either air drying or forced drying using warm air. However, if the temperature of the warm air is too high, there is a possibility that the enzyme contained in the solution might be deactivated. Thus, the temperature of the warm air preferably is around 50° C.

In the present invention, the material for the spacer is not particularly limited. For example, the same material as that for the insulating substrate can be used. The size of the spacer also is not particularly limited. For example, the spacer may have an overall length of 5 mm to 100 mm, a width of 3 mm to 50 mm, and a thickness of 0.01 mm to 1 mm; preferably an overall length of 10 mm to 50 mm, a width of 3 mm to 20 mm, and a thickness 0.05 mm to 0.5 mm; and more preferably an overall length of 15 mm to 30 mm, a width of 5 mm to 10 mm, and a thickness of 0.05 mm to 0.25 mm. The spacer has a cut-away portion that serves as a channel for leading blood. The cut-away portion may have, for example, an overall length of 1 mm to 30 mm and a width of 0.05 mm to 10 mm, preferably an overall length of 2 mm to 10 mm and a width of 0.3 mm to 5 mm, and more preferably an overall length of 2 mm to 10 mm and a width of 0.5 mm to 2 mm. The cut-away portion may be formed, for instance, by using a laser, a drill, or the like, or by forming the spacer using a die that can form the spacer provided with the cut-away portion.

In the present invention, the material for the cover is not particularly limited. For example, the same material as that for the insulating substrate can be used. It is more preferable that a portion of the cover corresponding to the ceiling of the sample supply channel is subject to a treatment for imparting hydrophilicity. The treatment for imparting hydrophilicity may be carried out by, for example, applying a detergent or introducing a hydrophilic functional group such as a hydroxyl group, a carbonyl group, or a carboxyl group to the cover surface by plasma processing or the like. The size of the cover is not particularly limited. For example, the cover may have an overall length of 5 mm to 100 mm, a width of 3 mm to 50 mm, and a thickness of 0.01 mm to 0.5 mm; preferably an overall length of 10 mm to 50 mm, a width of 3 mm to 20 mm, and a thickness of 0.05 mm to 0.25 mm; and more preferably an overall length of 15 mm to 30 mm, a width of 5 mm to 10mm, and a thickness of 0.05 mm to 0.1 mm. The cover preferably has an air vent hole, which may have, for example, a maximum diameter of 0.01 mm to 10 mm, preferably 0.05 mm to 5 mm, and more preferably 0.1 mm to 2 mm. The air vent hole may be formed, for instance, by perforating the cover with a laser, a drill, or the like, or by forming the cover using a die that can form the cover provided with the air vent hole.

This sensor can be produced by laminating the insulating substrate, the spacer, and the cover in this order and integrating them. The integration can be achieved by adhering these three components with an adhesive or through heat-sealing. As the adhesive, an epoxy adhesive, an acrylic adhesive, a polyurethane adhesive, a thermosetting adhesive (a hot melt adhesive or the like), a UV curable adhesive, or the like can be used, for example.

Measurement of blood glucose level using this sensor can be carried out in the following manner, for example. First, a fingertip or the like is punctured with a dedicated lancet to cause bleeding. On the other hand, the sensor is set in a dedicated measuring device (a meter). The blood inlet port of the sensor that is set in the measuring device is brought into contact with the blood that has come out, so that the blood is led to the analysis portion of the sensor by capillary action. In the analysis portion, glucose in the blood reacts with the oxidoreductase such as glucose oxidase contained in the reagent. On the other hand, after a lapse of a certain period after the detecting electrode detects the supply of the blood to the analysis portion, a constant voltage is applied between the working electrode and the counter electrode. As a result, a redox current flows. At this time, erythrocytes contained in the blood have been hemolyzed by the hemolyzing agent in the reagent portion 19, thereby releasing hemoglobin to the outside of the erythrocytes. The hemoglobin released to the outside reacts with the mediator, and a current generated by this reaction is detected by the electrodes simultaneously with the redox current. The detected current is measured by the measuring device, which converts the measured value into a glucose concentration and displays the value obtained by the conversion.

Figure 2:
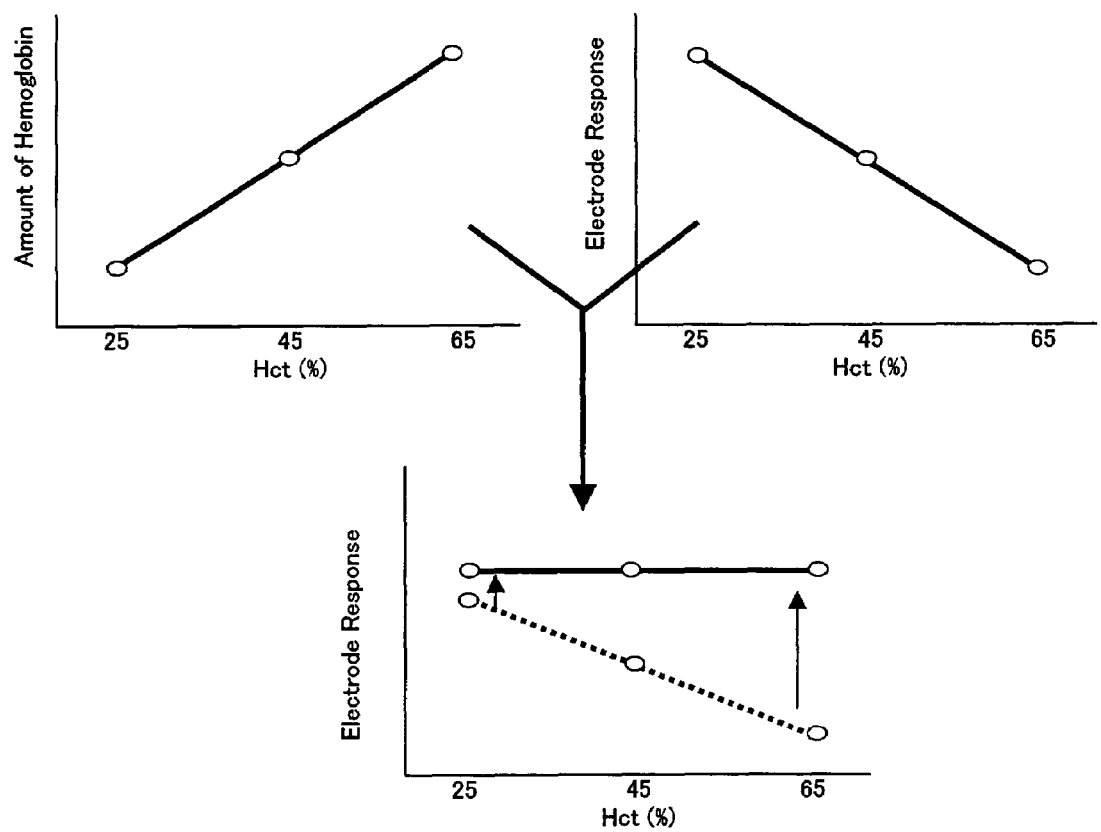
FIG. 2 is a view illustrating the principle of the present invention.

In the measurement using this sensor, the effect of Hct is corrected automatically. The reason for this will be described with reference to FIG. 2. As shown in the upper left graph of FIG. 2, an amount of hemoglobin in blood increases in keeping with Hct. Accordingly, an amount of reduced mediator generated by the electron exchange reaction between the hemoglobin and the mediator also increases. Although a reduced mediator generated by an enzyme reaction actually is to be measured, a reduced mediator also is generated through the above reaction, which causes an amperometric response obtained finally to become greater than it should be (hereinafter this phenomenon is referred to as a "positive error"). On the other hand, it has been known that an increase in Hct, i.e., an increase in blood cell (solid) components considerably affects the elementary processes (a nonuniform electron transfer reaction, diffusion, etc.) of the electrode reaction by electrode active species. Thus, an increase in Hct also causes the amperometric response obtained finally to become smaller than it should be (hereinafter this phenomenon is referred to as a "negative error"). In general, in a system without a membrane protein solubilizer, the above-described negative error is remarkable because solubilization of erythrocytes is not promoted in such a system. Thus, as shown in the upper right graph of FIG. 2, the amperometric response tends to decrease as Hct increases. On this account, by adding a membrane protein solubilizer to a sensor system so as to promote the solubilization of erythrocytes, it becomes possible to counterbalance the positive error and the negative error. As a result, it is possible to realize more accurate quantification of a blood component with the Hct value dependency of a sensor response being minimized (see the lower graph of FIG. 2).

Note here that the above sensor merely is an example of a sensor according to the present invention, and a sensor without a detecting electrode, for example, also falls within the scope of the present invention.

EXAMPLE 1

Hereinafter, examples of the present invention will be described along with a comparative example.

Sensors having the configuration as shown in FIG. 1 were produced in the manner described above. A reagent solution having the following composition was prepared, which was dropped on an analysis portion of each sensor and then dried to form a reagent portion.

(Composition of Reagent Portion)
enzyme (PQQ-GDH)
mediator (potassium ferricyanide)
hydrophilic polymer (CMC)
enzyme stabilizer (maltitol)
crystal homogenizing agent (taurine)
membrane protein solubilizer (sodium cholate: 1.2 mM)

On the other hand, from two types of human whole blood with glucose concentrations of 100 mg/dL and 400 mg/dL, six types of human whole blood samples were prepared by adjusting the Hct to 25%, 45%, and 65%.

Figure 3:
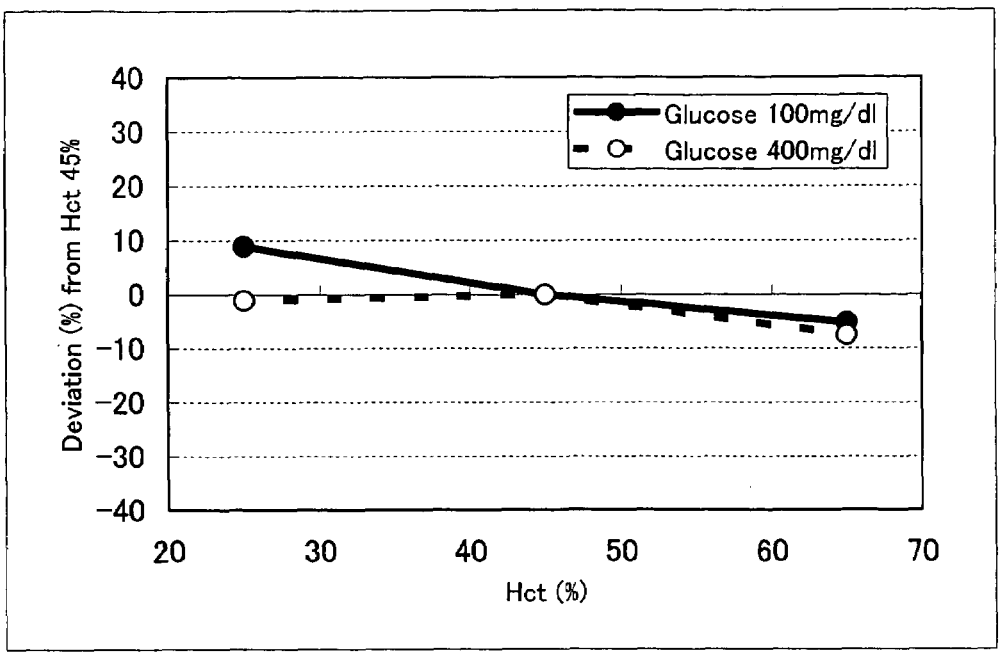
FIG. 3 is a graph showing the change in measured current with the change in Hct in an example of the present invention.

With regard to each sample, the measurement was carried out in the following manner. The sensor was set in a dedicated measuring device (a meter), and the blood inlet port of the sensor was brought into contact with the sample so that the sample was led to the analysis portion by capillary action. The measurement was started when the sample was detected by the detecting electrode. After a lapse of 3.5 seconds, a constant voltage of +0.2 V was applied between the working electrode and the counter electrode, and a current value after 1.5 seconds was measured. The number (n) of times the measurement was performed was n=10 with regard to each sample, and the average of the obtained measured values is shown in the graph of FIG. 3. In the graph of FIG. 3, the detected current with regard to each of the samples with the. Hct of 45% was set as a standard point, and the deviations (%) of the detected currents with regard to the samples with the other Hct values from this standard point are shown.

COMPARATIVE EXAMPLE

Figure 4:
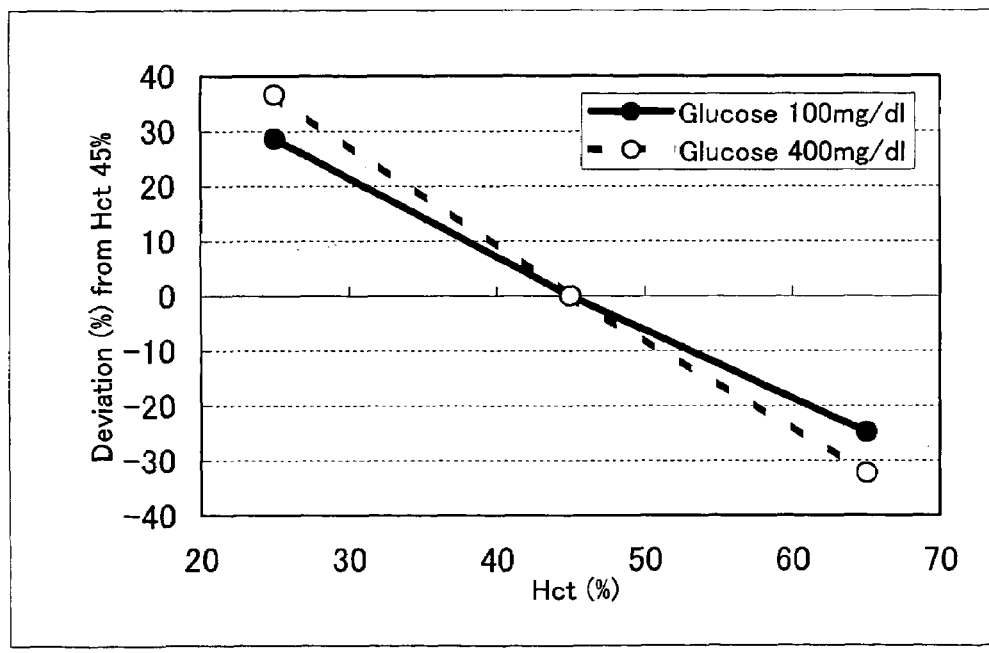
FIG. 4 is a graph showing the change in measured current with the change in Hct in a comparative example of the present invention.

Sensors were produced in the same manner as in Example 1 except that the hemolyzing agent was not used, and the measurement of current using these sensors was carried out in the same manner as in Example 1. The results are shown in the graph of FIG. 4. In the graph of FIG. 4, the detected current with regard to each of the samples with the Hct of 45% was set as a standard point, and the deviations (%) of the detected currents with regard to the samples with the other Hct values from this standard point are shown, as in the graph of FIG. 3.

As can be seen from the graph of FIG. 3, the current values obtained by the sensors according to Example 1 were substantially constant even under the varying Hct. In contrast, as can be seen from the graph of FIG. 4, the current values obtained by the sensors according to the comparative example varied greatly with the change in Hct.

EXAMPLE 2

Sensors were produced in the same manner as in Example 1. In these sensors, the reagent portion contained the same components as those in Example 1, but the amount of sodium cholate as the membrane protein solubilizer was changed. More specifically, in the present example, three types of sensors, namely, the sensor with 0.8 mM of sodium cholate, the sensor with 1.8 mM of sodium cholate, and the conventional sensor without the membrane protein solubilizer were produced.

Figure 5:
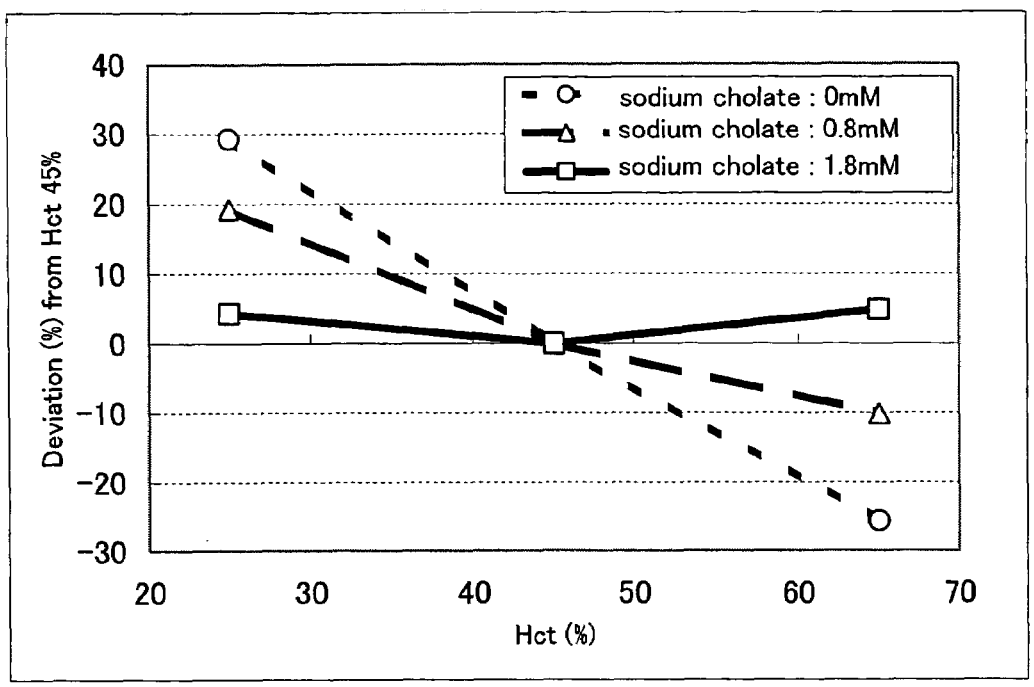
FIG. 5 is a graph showing the change in measured current with the change in Hct in another example of the present invention.

The measurement was carried out in the same manner as in Example 1. The conditions for the current measurement and the number (n) of times the measurement was performed also were the same as those in Example 1. FIG. 5 shows the results of the measurement performed with regard to three types of human whole blood samples prepared by adjusting the Hct of human whole blood with glucose concentration of 100 mg/dL to 25%, 45%, and 65%. In the graph of FIG. 5, the detected current with regard to the sample with the Hct of 45% was set as a standard point, and the deviations (%) of the detected currents with regard to the samples with the other Hct values from this standard point are shown.

As is clear from FIG. 5, the effect of Hct was reduced gradually with an increase in the concentration of the sodium cholate added to the reagent portion.

EXAMPLE 3

Sensors were produced in the same manner as in Example 1. In these sensors, the composition of the reagent portion was the same as in Example 1 except that the type of the membrane protein solubilizer was changed. More specifically, in the present example, three types of sensors respectively employing the following membrane protein solubilizers were produced.

(Membrane Protein Solubilizer)
sodium taurocholate (1.2 mM)
sodium taurodeoxycholate (1.2 mM)
sodium glycocholate (1.2 mM)

Figure 6:
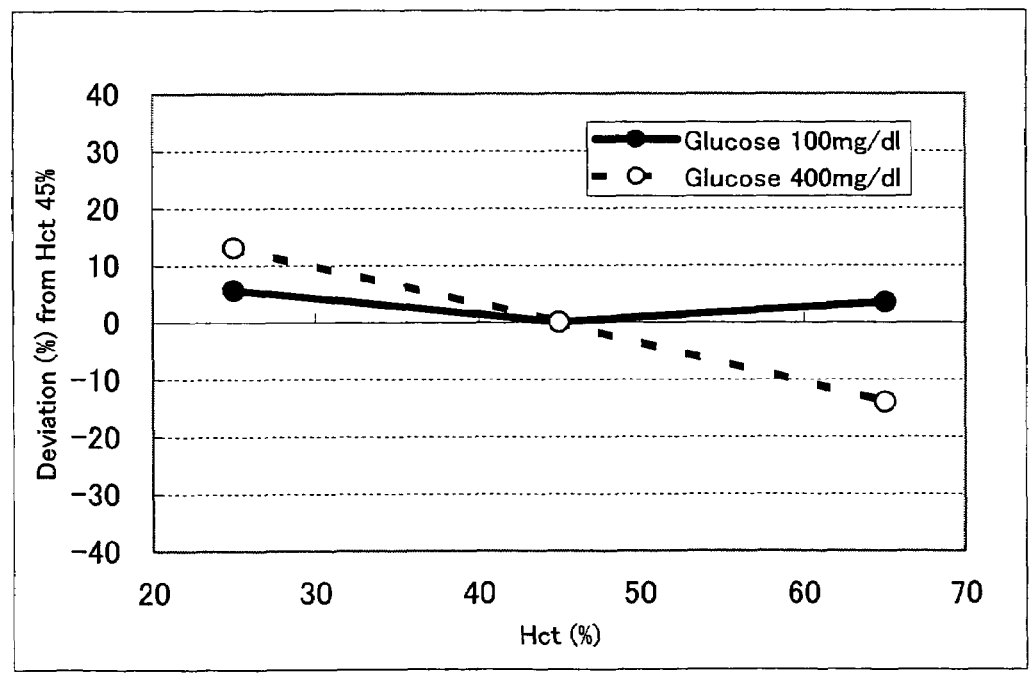
FIG. 6 is a graph showing the change in measured current with the change in Hct in the case where sodium taurocholate is added to a reagent solution in still another example of the present invention.
Figure 7:
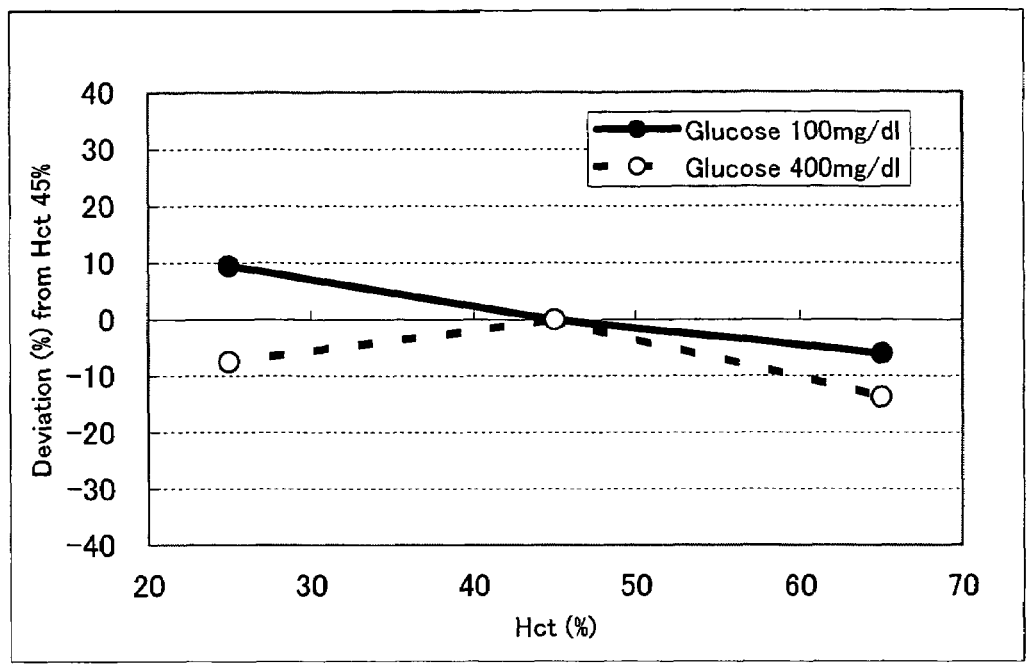
FIG. 7 is a graph showing the change in measured current with the change in Hct in the case where sodium taurodeoxycholate is added to a reagent solution in still another example of the present invention.
Figure 8:
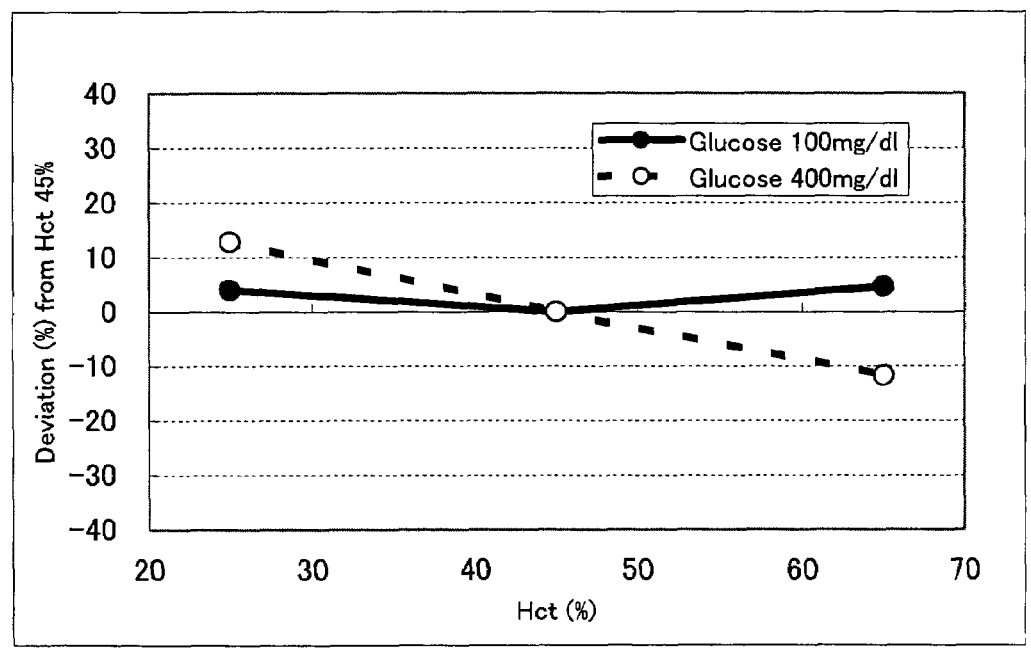
FIG. 8 is a graph showing the change in measured current with the change in Hct in the case where sodium glycocholate is added to a reagent solution in still another example of the present invention.

Using these sensors, the measurement was performed in the same manner as in Example 1 with regard to six types of human whole blood samples prepared by adjusting the Hct of two types of human whole blood with glucose concentrations of 100 mg/dL and 400 mg/dL to 25%, 45%, and 65%. FIG. 6 shows the result of the measurement using the sensor employing sodium taurocholate as the membrane protein solubilizer, FIG. 7 shows the result of the measurement using the sensor employing sodium taurodeoxycholate as the membrane protein solubilizer, and FIG. 8 shows the result of the measurement using the sensor employing sodium glycocholate as the membrane protein solubilizer. In the graphs of FIG. 6, FIG. 7, and FIG. 8, the detected current with regard to each of the samples with the Hct of 45% was set as a standard point, and the deviations (%) of the detected currents with regard to the samples with the other Hct values from this standard point are shown. In the present example, the conditions for the current measurement and the number (n) of times the measurement was performed also were the same as those in Example 1.

As clear from FIG. 6, FIG. 7, and FIG. 8 in comparison with FIG. 4 directed to a comparative example of Example 1, the membrane protein solubilizers used in the present example also could reduce the effect of Hct, as in the case of sodium cholate used in Example 1.

Although Examples 1, 2, and 3 are directed to a sensor for measuring a glucose concentration in blood, it is to be noted that an analyte or a measuring method is not limited thereto. For example, an analyte may be lactic acid, cholesterol, uric acid, or bilirubin. Moreover, although Examples 1, 2, and 3 are directed to an example where a current was measured using a sensor with a three-electrode structure including the working electrode 14, the counter electrode 15, and the detecting electrode 16 as shown in FIG. 1, it is to be noted that a sensor with a two-electrode structure without a detecting electrode also is within the scope of the present invention, and either of the three-electrode structure or the two-electrode structure may be used in the present invention. However, it is to be noted here that a sensor with three electrodes can achieve more accurate measurement than a sensor with two electrodes.

According to the measurement method and the sensor of the present invention, the effect of Hct can be corrected automatically and easily. Therefore, the measurement method and the sensor of the present invention are useful in measurement of a blood component.

Specific embodiments and examples described in the detailed description of the present invention are intended merely to clarify the technical details of the present invention. The present invention should not be limited to such specific examples to be understood narrowly. The present invention can be changed variously to be carried out within the spirit of the present invention and the range of the following claims.

What is claimed is:

1. A method of measuring a blood component, comprising:
bringing a sample containing blood into contact with a reagent containing an oxidoreductase that reacts with the blood component in the blood, a mediator, and a hemolyzing agent for hemolyzing an erythrocyte;
detecting a current generated by mixing of the sample and the reagent, the current being detected by electrodes; and
converting the detected current value into an amount of the blood component,
wherein the mixing of the sample and the reagent causes a redox reaction between the blood component in the blood and the oxidoreductase, hemolysis of the erythrocyte in the blood and a reaction between hemoglobin released to an outside of the erythrocyte and the mediator,
wherein detecting the current generated by mixing detects the current value that has been corrected to remove an effect of a hematocrit, and
wherein the amount of the blood component obtained by converting the detected current value is the blood component amount that has been corrected to remove the effect of the hematocrit.

2. The method according to claim 1, wherein the hemolyzing agent is a membrane protein solubilizer.

3. The method according to claim 2, wherein the membrane protein solubilizer is a cholic acid-based detergent.

4. The method according to claim 3, wherein the cholic acid-based detergent is at least one selected from the group consisting of cholic acid, sodium cholate, cholic acid methyl ester, chenodeoxycholic acid, sodium chenodeoxycholate, diphenylglycolic acid (benzilic acid), deoxycholic acid, sodium deoxycholate, sodium glycochenodeoxycholate, glycocholic acid, sodium glycocholate, glycodeoxycholic acid, sodium glycodeoxycholate, glycolic acid, sodium glycolate, sodium glycolithocholate, lithocholic acid, sodium thioglycolate, sodium taurocholate, sodium taurodeoxycholate, sodium tauroursodeoxycholate, sodium ursodeoxycholate, and ursodeoxycholic acid.

5. The method according to claim 2, wherein an amount of the membrane protein solubilizer is 0.01 mM to 100 mM per one measurement.

6. The method according to claim 1, wherein the mediator is potassium ferricyanide.

7. The method according to claim 1, wherein the blood component as an analyte is at least one selected from the group consisting of glucose, lactic acid, uric acid, bilirubin, and cholesterol.

8. The method according to claim 1, wherein the blood component as an analyte is glucose, and the oxidoreductase is at least one of glucose oxidase and glucose dehydrogenase.

9. A sensor for measuring a blood component, comprising an analysis portion., the analysis portion comprising:
- a working electrode:
- a counter electrode; and
- a reagent portion, the reagent portion comprising (1) an oxidoreductase that reacts with the blood components, (2) a mediator, and (3) a hemolyzing agent for hemolyzing an erythrocyte,
- wherein within the analysis portion, the erythrocyte is hemolyzed with the hemolyzing agent, a redox reaction is caused between the blood component and the oxidoreductase in the presence of the mediator, a reaction is caused between hemoglobin released to an outside of an erythrocyte by the hemolysis and the mediator, and a current generated by the redox reaction and the reaction between the hemoglobin and the mediator is detected by the working electrode and the counter electrode, whereby an amount of the blood component that has been corrected to remove an effect of a hematocrit can be measured.

10. The sensor according to claim 9, wherein the hemolyzing agent is a membrane protein solubilizer.

11. The sensor according to claim 10, wherein the membrane protein solubilizer is a cholic acid-based detergent.

12. The sensor according to claim 11, wherein the cholic acid-based detergent is at least one selected from the group consisting of cholic acid), sodium cholate, cholic acid methyl ester, chenodeoxycholic acid, sodium chenodeoxycholate, diphenylglycolic acid (benzilic acid), deoxycholic acid, sodium deoxycholate, sodium glycochenodeoxycholate, glycocholic acid, sodium glycocholate, glycodeoxycholic acid, sodium glycodeoxycholate, glycolic acid, sodium glycolate, sodium glycolithocholate, lithocholic acid, sodium thioglycolate, sodium taurocholate, sodium taurodeoxycholate, sodium tauroursodeoxycholate, sodium ursodeoxycholate, and ursodeoxycholic acid.

13. The sensor according to claim 10, wherein an amount of the membrane protein solubilizer is 0.01 mM to 100 mM per one sensor.

14. The sensor according to claim 9, wherein the mediator is potassium ferricyanide.

15. The sensor according to claim 9, wherein the blood component as an analyte is at least one selected from the group consisting of glucose, lactic acid, uric acid, bilirubin, and cholesterol.

16. The sensor according to claim 9, wherein the blood component as an analyte is glucose, and the oxidoreductase is at least one of glucose oxidase and glucose dehydrogenase.

17. The sensor according to claim 9, wherein the reagent portion further comprises a hydrophilic polymer, an enzyme stabilizer, and a crystal homogenizing agent.

18. The sensor according to claim 9, further comprising an insulating substrate, wherein the working electrode and the counter electrode are disposed on the insuiating substrate, thereby forming the analysis portion, the reagent portion is disposed on the analysis portion, the analysis portion communicates with one end of a channel for leading blood to the analysis portion, and the other end of the channel is open toward an outside of the sensor, thereby allowing this opening to serve as a blood supply port.

19. The sensor according to claim 18, further comprising a spacer and a cover, wherein the cover is disposed on the insulating substrate with the spacer intervening between the cover and the insulating substrate.

20. The sensor according to claim 9, further comprising a detecting electrode, wherein the detecting electrode is located farther from the blood inlet port than the analysis portion, and whether or not blood is supplied to the analysis portion is detected by the detecting electrode.

21. A method of measuring a blood component, comprising:
- hemolyzing an erythrocyte in blood so as to cause hemoglobin to be released to an outside of the erythrocyte;
- causing a redox reaction between the blood component and an oxidoreductase in the presence of a mediator so as to cause the hemoglobin released to the outside of the erythrocyte to react with the mediator;
- detecting a current generated by the redox reaction and the reaction between the hemoglobin and the mediator by electrodes, and
- converting the detected current value into an amount of the blood component, whereby the blood component amount that has been corrected to remove an effect of a hematocrit is measured.

* * * * *